United States Patent [19]

Hutchinson et al.

[11] Patent Number: 5,364,781
[45] Date of Patent: Nov. 15, 1994

[54] PROCESS FOR PREPARING DAUNORUBICIN

[75] Inventors: Charles R. Hutchinson, Madison, Wis.; Krishna M. Madduri, Andhra Pradesh, India; Francesca Torti; Anna L. Colombo, both of Milan, Italy

[73] Assignee: Farmitalia Carlo ERBA S.r.l, Milan, Italy

[21] Appl. No.: 959,941

[22] Filed: Oct. 9, 1992

Related U.S. Application Data

[63] Continuation-in-part of Ser. No. 793,873, Nov. 18, 1991, abandoned.
[51] Int. Cl.$^5$ .............................................. C12N 9/10
[52] U.S. Cl. .................................. 435/193; 435/886; 435/888; 536/23.2; 930/240; 935/14
[58] Field of Search ................ 435/69.1, 193, 78, 886, 435/888; 530/412, 350; 430/240; 536/23.2

[56] References Cited

PUBLICATIONS

Bradshaw et al. (eds.) 1990, in: *Proteins: Form and Function*, Elsevier Trends J. Cambridge. (Elsevier Sci. Publ.) pp. 1–19.

Connors et al. 1990, J. Gen. Microbiol., 136, 1895–1898.

*Primary Examiner*—Christopher S. F. Low
*Attorney, Agent, or Firm*—Nikaido, Marmelstein, Murray & Oram

[57] ABSTRACT

The ability to convert carminomycin to daunorubicin can be conferred on a host by transforming the host with a recombinant vector comprising a DNA having the configuration of restriction sites shown in FIGS. 2, 3 & 4 and nucleotide sequence shown in FIG. 3 of the accompanying drawings or a restriction fragment derived therefrom containing a gene coding for carminomycin 4-O-methyltransferase.

1 Claim, 6 Drawing Sheets

Fig. 3a (SEQ ID NO: 1)

```
          S
          p
          h
          I
      GCATGCCGGCAACCGGGCGCCGGTTCTCCGGTGAGCAGATCCACCTCATCCGCATCGTC
  2   ---+---------+---------+---------+---------+---------+-----  60
      CGTACGGCCGTTGGCCCGCGGCCAAGAGGCCACTCGTCTAGGTGGAGTAGGCGTAGCAG

GACGGCAAGATCCGCGATCACCGCGACTGGCCCGACTACCTCGGCACCTACCGCCAGCTC
 61   ----+---------+---------+---------+---------+---------+----- 120
      CTGCCGTTCTAGGCGCTAGTGGCGCTGACCGGGCTGATGGAGCCGTGGATGGCGGTCGAG

GGCGAGCCCTGGCCCACCCCCGAGGGCTGGCGCCCCTGACCCCCCATCACCCCGCCGACG
121   ----+---------+---------+---------+---------+---------+----- 180
      CCGCTCGGGACCGGGTGGGGGCTCCCGACCGCGGGGACTGGGGGGTAGTGGGGCGGCTGC

CCACGACAGGAGCACGGACACACCATGACAGCCGAACCGACGGTCGCGGCCCGGCCGCAG
181   ----+---------+---------+---------+---------+---------+----- 240
      GGTGCTGTCCTCGTGCCTGTGTGGTACTGTCGGCTTGGCTGCCAGCGCCGGGCCGGCGTC

N
                                                         c
                                                         o
                                                         I
      CAGATCGACGCCCTCAGGACCCTGATCCGCCTCGGAAGCCTGCACACGCCCATGGTCGTC
241   ----+---------+---------+---------+---------+---------+----- 300
      GTCTAGCTGCGGGAGTCCTGGGACTAGGCGGAGCCTTCGGACGTGTGCGGGTACCAGCAG

CGGACGGCCGCCACCCTGCGGCTCGTCGACCACATCCTGGCCGGGGCCCGCACCGTGAAG
301   ----+---------+---------+---------+---------+---------+----- 360
      GCCTGCCGGCGGTGGGACGCCGAGCAGCTGGTGTAGGACCGGCCCCGGGCGTGGCACTTC

GCCCTGGCGGCCAGGACAGACACCCGGCCGGAAGCACTCCTGCGACTGATCCGCCACCTG
361   ----+---------+---------+---------+---------+---------+----- 420
      CGGGACCGCCGGTCCTGTCTGTGGGCCGGCCTTCGTGAGGACGCTGACTAGGCGGTGGAC

X
                      h
                      o
                      I
      GTGGCGATCGGACTGCTCGAGGAGGACGCACCGGGCGAGTTCGTCCCGACCGAGGTCGGC
421   ----+---------+---------+---------+---------+---------+----- 480
      CACCGCTAGCCTGACGAGCTCCTCCTGCGTGGCCCGCTCAAGCAGGGCTGGCTCCAGCCG

GAGCTGCTCGCCGACGACCACCCAGCCGCGCAGCGTGCCTGGCACGACCTGACGCAGGCC
481   ----+---------+---------+---------+---------+---------+----- 540
      CTCGACGAGCGGCTGCTGGTGGGTCGGCGCGTCGCACGGACCGTGCTGGACTGCGTCCGG

GTGGCGCGCGCCGACATCTCCTTCACCCGCCTCCCCGACGCCATCCGTACCGGCCGCCCC
541   ----+---------+---------+---------+---------+---------+----- 600
      CACCGCGCGCGGCTGTAGAGGAAGTGGGCGGAGGGGCTGCGGTAGGCATGGCCGGCGGGG

ACGTACGAGTCCATCTACGGCAAGCCGTTCTACGAGGACCTGGCCGGCCGCCCCGACCTG
601   ----+---------+---------+---------+---------+---------+----- 660
      TGCATGCTCAGGTAGATGCCGTTCGGCAAGATGCTCCTGGACCGGCCGGCGGGGCTGGAC
```

Fig. 3b

```
       CGCGCGTCCTTCGACTCGCTGCTCGCCTGCGACCAGGACGTCGCCTTCGACGCTCCGGCC
661    ----+---------+---------+---------+---------+---------+----- 720
       GCGCGCAGGAAGCTGAGCGACGAGCGGACGCTGGTCCTGCAGCGGAAGCTGCGAGGCCGG

GCCGCGTACGACTGGACGAACGTCCGGCATGTGCTCGACGTGGGTGGCGGCAAGGGTGGT
721    ----+---------+---------+---------+---------+---------+----- 780
       CGGCGCATGCTGACCTGCTTGCAGGCCGTACACGAGCTGCACCCACCGCCGTTCCCACCA

TTCGCCGCGGCCATCGCGCGCCGGGCCCCGCACGTGTCGGCCACCGTGCTGGAGATGGCG
781    ----+---------+---------+---------+---------+---------+----- 840
       AAGCGGCGCCGGTAGCGCGCGGCCCGGGGCGTGCACAGCCGGTGGCACGACCTCTACCGC

GGCACCGTGGACACCGCCCGCTCCTACCTGAAGGACGAGGGCCTCTCCGACCGTGTCGAC
841    ----+---------+---------+---------+---------+---------+----- 900
       CCGTGGCACCTGTGGCGGGCGAGGATGGACTTCCTGCTCCCGGAGAGGCTGGCACAGCTG

GTCGTCGAGGGGGACTTCTTCGAGCCGCTGCCCCGCAAGGCGGACGCGATCATCCTCTCT
901    ----+---------+---------+---------+---------+---------+----- 960
       CAGCAGCTCCCCCTGAAGAAGCTCGGCGACGGGGCGTTCCGCCTGCGCTAGTAGGAGAGA
                                                B
                                                a
                                                m
                                                H
                                                I
       TTCGTCCTCCTCAACTGGCCGGACCACGACGCCGTCCGGATCCTCACCCGCTGCGCCGAG
961    ----+---------+---------+---------+---------+---------+----- 1020
       AAGCAGGAGGAGTTGACCGGCCTGGTGCTGCGGCAGGCCTAGGAGTGGGCGACGCGGCTC

GCCCTGGAGCCCGGCGGGCGCATCCTGATCCACGAGCGCGACGACCTCCACGAGAACTCG
1021   ----+---------+---------+---------+---------+---------+----- 1080
       CGGGACCTCGGGCCGCCCGCGTAGGACTAGGTGCTCGCGCTGCTGGAGGTGCTCTTGAGC
                         S
                         s
                         t
                         I
       TTCAACGAACAGTTCACAGAGCTCGATCTGCGGATGCTGGTCTTCCTCGGCGGTGCCCTG
1081   ----+---------+---------+---------+---------+---------+----- 1140
       AAGTTGCTTGTCAAGTGTCTCGAGCTAGACGCCTACGACCAGAAGGAGCCGCCACGGGAC

CGCACCCGCGAGAAGTGGGACGGCCTGGCCGCGTCGGCGGGCCTCGTGGTCGAGGAGGTG
1141   ----+---------+---------+---------+---------+---------+----- 1200
       GCGTGGGCGCTCTTCACCCTGCCGGACCGGCGCAGCCGCCCGGAGCACCAGCTCCTCCAC

CGGCAACTGCCGTCGCCGACCATCCCGTACGACCTCTCGCTCCTCGTCCTTGCCCCCGCG
1200   ----+---------+---------+---------+---------+---------+----- 1260
       GCCGTTGACGGCAGCGGCTGGTAGGGCATGCTGGAGAGCGAGGAGCAGGAACGGGGCGCG

GCCACCGGCGCCTGACACACGAGGTACGGGAAGGGTTCATCAGCAATGCCGACACGCATG
1261   ----+---------+---------+---------+---------+---------+----- 1320
       CGGTGGCCGCGGACTGTGTGCTCCATGCCCTTCCCAAGTAGTCGTTACGGCTGTGCGTAC

ATCACCAACGATGAGGTGACCCTGTGGAGCGAAGGGCTCGGCGATCCGGCCGACGCCCCG
1321   ----+---------+---------+---------+---------+---------+----- 1380
       TAGTGGTTGCTACTCCACTGGGACACCTCGCTTCCCGAGCCGCTAGGCCGGCTGCGGGGC
```

Fig. 3c

```
     TTGCTCCTGATCGCCGGCGGCAACCTCTCGGCCAAATCGTGGCCGGACGAGTTCGTCGAA
1381 ----+---------+---------+---------+---------+---------+----- 1440
     AACGAGGACTAGCGGCCGCCGTTGGAGAGCCGGTTTAGCACCGGCCTGCTCAAGCAGCTT

CGCCTGGTCGCGGCCGGGCACTTCGTGATCCGCTACGACCACCGGGACACCGGGCGCTCC
1441 ----+---------+---------+---------+---------+---------+----- 1500
     GCGGACCAGCGCCGGCCCGTGAAGCACTAGGCGATGCTGGTGGCCCTGTGGCCCGCGAGG

TCCCGGTGCGACTTCGCGCTCCACCCCTACGGCTTCGACGAGCTGGCCGCCGACGCGCTG
1501 ----+---------+---------+---------+---------+---------+----- 1560
     AGGGCCACGCTGAAGCGCGAGGTGGGGATGCCGAAGCTGCTCGACCGGCGGCTGCGCGAC

GCCGTCCTGGACGGCTGGCAGGTCCGCGCCGCCCATGTGGTGGGCATGTCGCTGGGCAAC
1561 ----+---------+---------+---------+---------+---------+----- 1620
     CGGCAGGACCTGCCGACCGTCCAGGCGCGGCGGGTACACCACCCGTACAGCGACCCGTTG

P
                 v
                 u
                 I
                 I
     ACCATCGGCCAGC
1621 ----+-------- 1630
     TGGTAGCCGGTCG
```

Deduced amino acid sequence of carminomycin 4-O-methytransferase
(SEQ ID NO:2)

```
  1  MTAEPTVAAR  PQQIDALRTL  IRLGSLHTPM  VVRTAATLRL  VDHILAGART

51  VKALAARTDT  RPEALLRLIR  HLVAIGLLEE  DAPGEFVPTE  VGELLADDHP

101  AAQRAWHDLT  QAVARADISF  TRLPDAIRTG  RPTYESIYGK  PFYEDLAGRP

151  DLRASFDSLL  ACDQDVAFDA  PAAAYDWTNV  RHVLDVGGGK  GGFAAAIARR

201  APHVSATVLE  MAGTVDTARS  YLKDEGLSDR  VDVVEGDFFE  PLPRKADAII

251  LSFVLLNWPD  HDAVRILTRC  AEALEPGGRI  LIHERDDLHE  NSFNEQFTEL

301  DLRMLVFLGG  ALRTREKWDG  LAASAGLVVE  EVRQLPSPTI  PYDLSLLVLA

351  PAATGA*
```

Fig. 4

PROCESS FOR PREPARING DAUNORUBICIN

CROSS REFERENCE TO RELATED APPLICATION

This is a continuation-in-part application U.S. Ser. No. 07/793,873, filed Nov. 18, 1991 abandoned.

FIELD OF THE INVENTION

The present invention concerns a way to produce anthracyclines useful in the treatment of cancer by modifying the biosynthesis of daunorubicin so as to improve the production of daunorubicin from carminomycin in streptomycetes other than *Streptomyces peucetius* 29050 and in bacterial cell extracts or by purified enzymes derived therefrom.

BACKGROUND OF THE INVENTION

The anthracyclines of the daunorubicin group, such as doxorubicin, carminomycin and aclacinomycin, are among the most widely employed agents in antitumoral therapy [F. Arcamone, *Doxorubicin*, Academic Press, New York, 1981, pp. 12–25; A. Grein, *Process Biochem.* 16:34 (1981); T. Kaneko, Chimicaoggi May 11, (1988)]. Improved derivatives of daunorubicin and doxorubicin have been made by chemical synthesis to enhance their antitumor activity, particularly by the oral route of administration, and to combat the acute toxicity and chronic cardiotoxicity associated with the use of these drugs in the treatment of cancer [Penco, *Process Biochem.* 15:12 (1980); T. Kaneko, Chimicaoggi May 11, (1988)]. 4'-Epidoxorubicin (Epirubicin ®) and 4-demethoxydaunorubicin (Idarubicin ®) are examples of such analogs.

These naturally occuring compounds are produced by various strains of Streptomyces (*S. peucetius, S. coeruleorubidus, S. galilaeus, S. griseus, S. griseoruber, S. insignis, S. viridochromogenes, S. bifurcus* and Streptomyces sp. strain C5) and by *Actinomyces carminata*. Doxorubicin is only produced by *S. peucetius* subsp. *caesius* but daunorubicin is produced by *S. peucetius* as well as the other Streptomyces described above. The type strains *S. peucetius* subsp. *caesius* IMRU 3920 (this strain is the same as ATCC 27952 and hereinafter is abbreviated to "*S. peucetius* 3920"), *S. peucetius* ATCC 29050 ("*S. peucetius* 29050"), and *S. peucetius* subsp. *caesius* ATCC 27952 ("*S. peucetius* 27952") are publically available and are described in U.S. Pat. No. 3,590,028. *S. peucstius* 29050 and 27952 have been deposited at the American Type Culture Collection, Rockville, Md. USA, receiving the index number ATCC 29050 and 27952.

Figure 1:
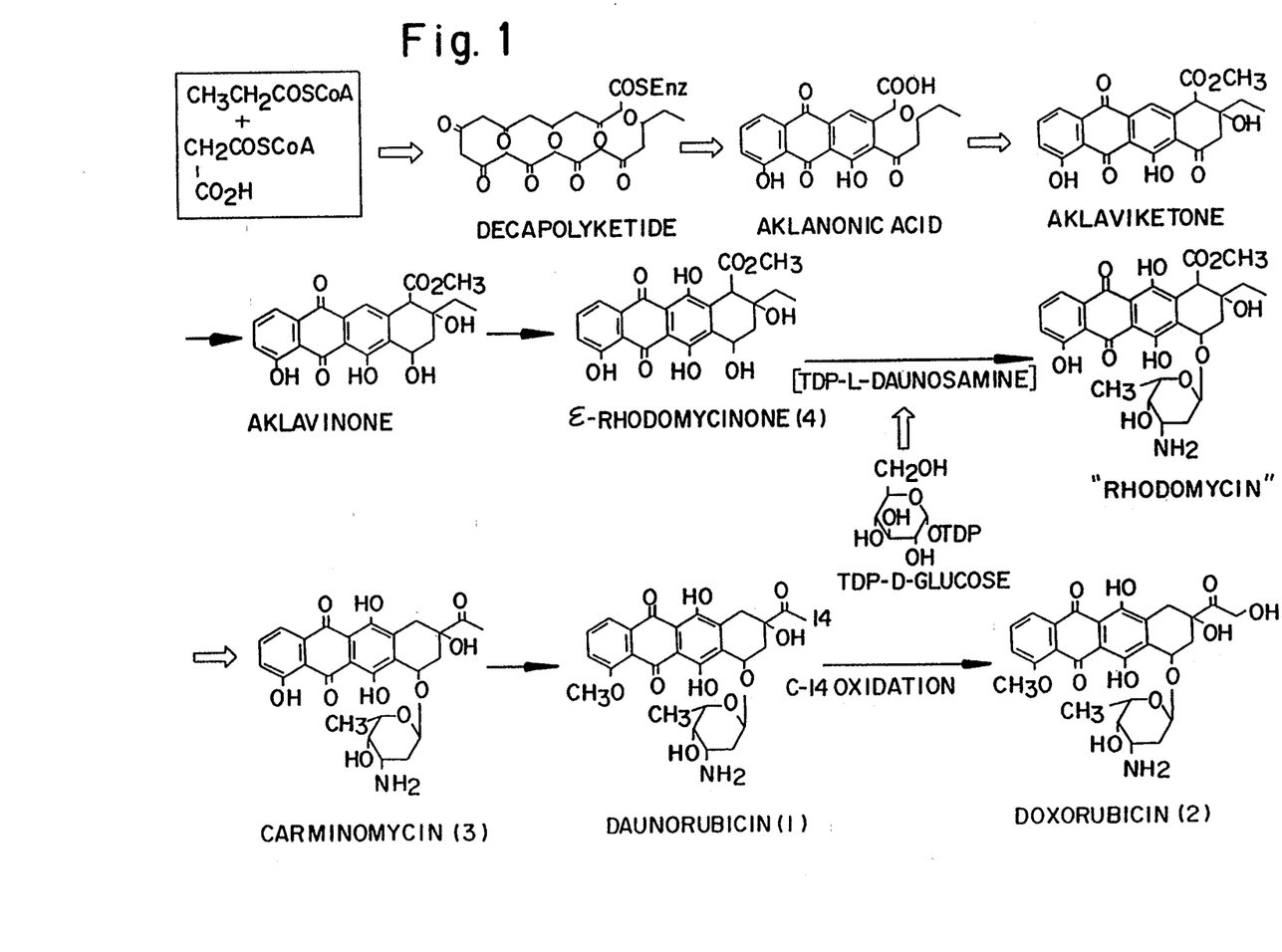
FIG. 1 is a summary of the doxorubicin biosynthetic pathway.

The anthracycline doxorubicin (2) is made by *S. peucetius* 27952 from malonic acid, propionic acid, and glucose by the pathway shown in FIG. 1 of the accompanying drawings. ε-Rhodomycinone (4), carminomycin (3) and daunorubicin (1) are established intermediates in this process [Grein, *Advan. Appl. Microbiol.* 32:203 (1987), Eckardt and Wagner, *J. Basic Microbiol.* 28:137 (1988)]. Two steps in this pathway involve the O-methylation of discrete intermediates: the conversion of aklanonic acid to methyl aklanonate and carminomycin (3) to daunorubicin (1). Cell-free extracts of *S. peucetius* 29050, *S. insignis* ATCC 31913, *S. coeruleorubidus* ATCC 31276 and Streptomyces sp. C5 have been shown to catalyze the latter step in the presence of S-adenosyl-L-methionine [Connors et al., *J. Gen. Microbiol.* 136:1895 (1990)], suggesting that all of these strains contain a specific carminomycin 4-O-methyltransferase (COMT protein).

Genes for daunorubicin biosynthesis and daunorubicin resistance have been obtained from *S. peucetius* 29050 and *S. peucetius* 27952 by cloning experiments [Stutzman-Engwall and Hutchinson, *Proc. Natl. Acad. Sci. USA* 86:3135 (1988); Otten et al., *J. Bacteriol.* 172:3427 (1990)]. These studies have shown that, when introduced into *Streptomyces lividans* 1326, these cloned genes confer the ability to produce ε-rhodomycinone and to become resistant to daunorubicin and doxorubicin to this host. In subsequent work we examined whether these clones could confer the ability to convert carminomycin to daunorubicin when introduced into *S. lividans*. We have now isolated a 1.6 kilobase (kb) DNA segment that incorporates the carminomycin 4-O-methyltransferase gene, which hereinafter will be abbreviated as "dnrK".

SUMMARY OF THE INVENTION

Figure 2:
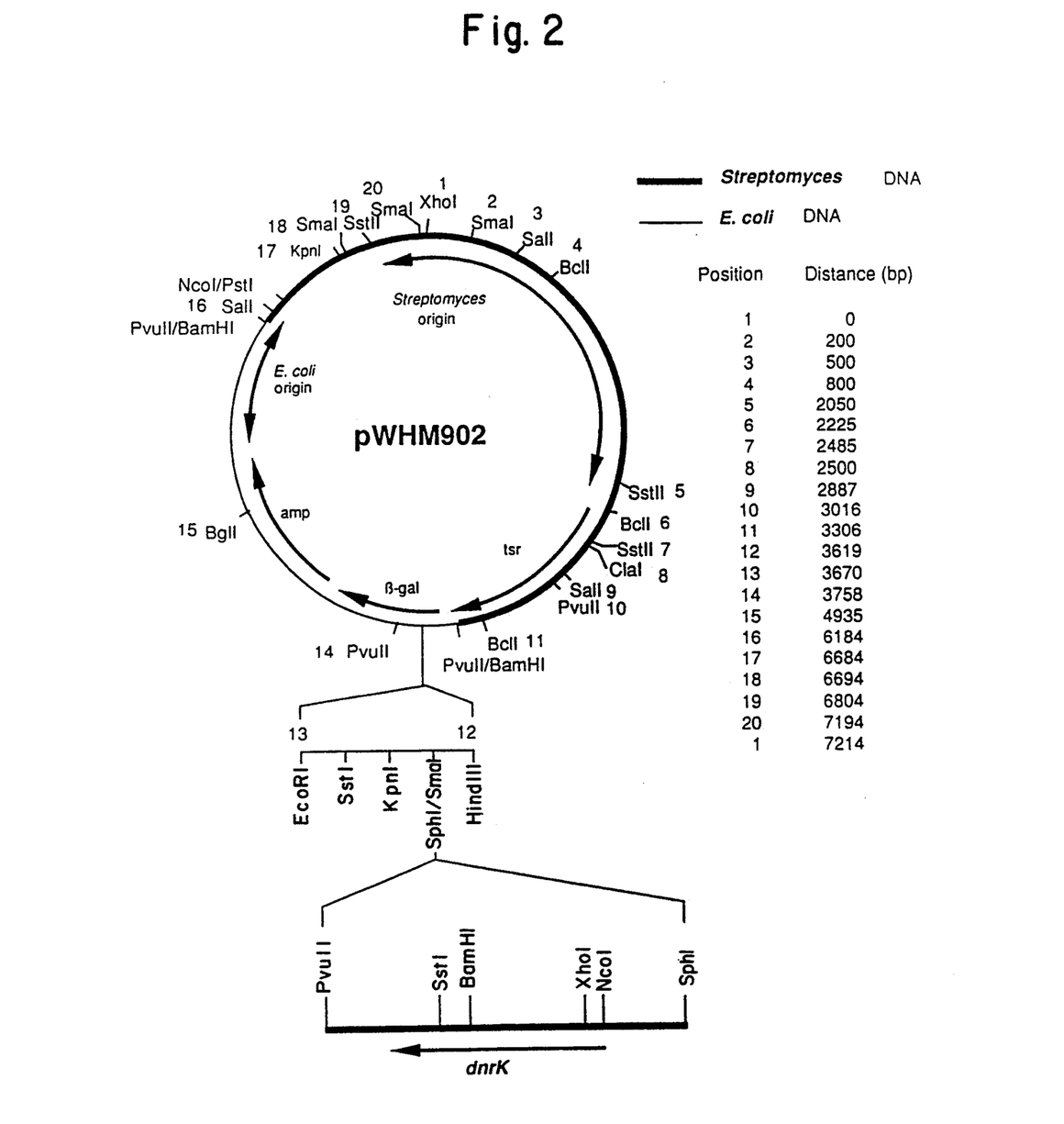
FIG. 2 is the restriction map analysis of the first DNA of the invention. This is an insert in recombinant plasmid pWHM902 That was constructed by insertion of a 1.6 kb SphI/PvuII DNA fragment containing the carminomycin 4-O-methyltransferase (dnrK) gone, which was obtained from recombinant plasmid pWHM901 by its digestion with SphI and PvuII, into the SphI/SmaI sites of the pWHM3 plasmid, an *Escherichia coli*-Streptomyces shuttle vector [Vara et al., *J. Bacteriol.* 171:5872 (1989)]. The map shown in FIG. 2 does not necessarily provide an exhaustive listing of all restriction sites present in the DNA segment. However, the reported sites are sufficient for an unambiguous recognition of the segments.

The present invention provides DNAs having the configuration of restriction sites shown in FIG. 2 of the accompanying drawings or a restriction fragment derived therefrom containing a gene, dnrK, coding for carminomycin 4O-methyltransferase. For convenience, the DNA segment shown in FIG. 2 is called here "insert DNA" and is further defined by the DNA sequence shown in FIG. 3 of the accompanying drawings. The invention also provides:

(1) recombinant vectors that are capable of transforming a host cell and that contain an insert DNA or a restriction fragment derived therefrom containing the dnrK gene;

(2) recombinant vectors that are able to increase the number of copies of the dnrK gene and the amount of its product in a strain of Streptomyces spp. producing daunorubicin;

(3) recombinant vectors that are able to express the dnrK gene in *Escherichia coli* so as to enable the production of the purified carminomycin 4-O-methyltransferase enzyme.

(4) a microbial source of carminomycin 4-O-methyltransferase for the bioconversion of carminomycin into pure daunorubicin.

BRIEF DESCRIPTION OF THE DRAWINGS

FIGS. 3a, 3b and 3c are a schematic illustration of a nucleotide sequence of the dnrK DNA segment which corresponds to that encoding carminomycin 4-O-methyltransferase. This covers the region between the SphI and the PvuII restriction sites of pWHM902 and shows the coding strand in the 5'to 3'direction. The derived amino acid sequence of the translated open reading frame encoding carminomycin 4-O-methyltransferase is shown below the nucleotide sequence of the dnrK gene. (SEQ ID NO:1, SEQ ID NO:2)

DETAILED DESCRIPTION OF THE INVENTION

The insert DNAs and restriction fragments of the invention contain a gene (dnrK) coding for carminomycin 4-O-methyltransferase. For such a gene to be expressed, the DNA may carry its own transcriptional control sequence and, in particular, its own promoter which is operably connected to the gene and which is recognised by a host cell RNA polymerase. Alternatively, the insert DNA or restriction fragment may be ligated to another transcriptional control sequence in the correct fashion or cloned into a vector at a restriction site appropriately located neighboring a transcriptional control sequence in the vector.

An insert DNA or restriction fragment carrying a carminomycin 4-O-methyltransferase gene may be cloned into a recombinant DNA cloning vector. Any autonomously replicating and/or integrating agent comprising a DNA molecule to which one or more additional DNA segments can be added may be used. Typically, however, the vector is a plasmid. A preferred plasmid is The high copy number plasmid pWHM3 or pIJ702 [Katz et al., J. Gen. Microbiol. 129:2703 (1983)]. Other suitable plasmids are pIJ385 [Mayeri et al., J. Bacteriol. 172:6061 (1990)], pIJ680 (Hopwood et al., Genetic Manipulation of Streptomyces. A laboratory Manual, John Innes Foundation, Norwich, UK, 1985), pWHM601 [Guilfoile and Hutchinson, Proc. Natl. Acad. Sci. USA 88:8553 (991)] or pPM927 [Smokina et al., Gene 94:52 (1990)]. Any suitable technique may be used to insert the insert DNA or restriction fragment thereof into the vector. Insertion can be achieved by ligating the DNA into a linearized vector at an appropriate restriction site. For this, direct combination of sticky or blunt ends, homopolymer tailing, or the use of a linker or adapter molecule may be employed.

The recombinant vector is used to transform a suitable host cell. The host cells may be ones that are carminomycin- or daunorubicin-sensitive, i.e., cannot grow in the presence of a certain amount of carminomycin or daunorubicin, or that are carminomycin- or daunorubicin-resistant. The host may be a microorganism. Strains of S. peucetius, in particular S. peucetius 29050, and other strains of Streptomyces species that produce anthracyclines or do not produce them may therefore be transformed. Transformants of Streptomyces strains are typically obtained by protoplast transformation. The dnrK gene may also be incorporated into other vectors and expressed in non-streptomycetes like E. coli. The COMT protein obtained by the transformed host may be employed for bioconverting carminomycin to daunorubicin. This method would allow the preparation of highly pure daunorubicin starting from a cell extract produced by a fermentation process and containing the undesired intermediate carminomycin besides the daunorubicin.

The bioconversion process can be carried out either by using directly the free or immobilized transformed cells or by isolating the COMT protein, which can be used in the free form, immobilized according to known Techniques to resins, glass, cellulose or similar substances by ionic or covalent bonds, or grafted to fibers permeable to the substrate or insolubilized by cross-linkage. The COMT protein may also be used in the raw cellular extract.

The recombinant vector of The present invention may be also used to transform a suitable host cell, which produces daunorubicin, in order to enhance The bioconversion of carminomycin and to minimize The presence of said unwanted intermediate into the final cell extract. The host cells may be ones that are carminomycin, daunorubicin- or doxorubicin-resistant, i.e., can grow in the presence of any amount of carminomycin, daunorubicin or doxorubicin. Strains of S. peucetius, in particular S. peucetius 29050, and other strains of Streptomyces species that produce anthracyclines may therefore be transformed. Transformants of Streptomyces strains are typically obtained by protoplast transformation. Daunorubicin can be obtained by culturing a transformed strain of S. peucetius or another Streptomyces species that does not contain a dnrK gene and recovering The daunorubicin or related anthracyclines thus-produced.

The insert DNAs are obtained from the genomic DNA of S. peucetius 29050. This strain has been deposited at the American Type Culture Collection, Rockville, Md., USA under the accession number ATCC 29050. A strain derived from S. peucetius 29050, like S. peucetius 27952, may also be used, which typically will also be able to convert carminomycin to daunorubicin. Insert DNAs may therefore be obtained by:

(a) preparing a library of the genomic DNA of S. peucetius 29050 or a strain derived therefrom;
(b) screening the library for clones with the ability to convert carminomycin to daunorubicin;
(c) obtaining an insert DNA from a recombinant vector that forms part of the library and That has been screened as positive for The ability to convert carminomycin to daunorubicin; and
(d) optionally, obtaining from the insert DNA a restriction fragment that contains a gene coding for carminomycin 4-O-methyltransferase.

The library may be prepared in step (a) by partially digesting the genomic DNA of S. peucetius 29050 or a strain derived Therefrom. The restriction enzyme MboI is perferably used. The DNA fragments Thus obtained can, be size fractionated: fragments from 3 to 5 kb in size are preferred. These fragments are ligated into a linearized vector such as pWHM3 or pIJ702. Host cells are Transformed with the ligation mixture. Typically, the host cells can not produce carminomycin or daunorubicin and can be carminomycin- or daunorubicin-sensitive, for example, sensitive to 10 microgram or less of carminomycin or daunorubicin per ml. For example, S. lividans JI1623 protoplasts (Hopwood et al., Genetic Manipulation of Streptomyces. A Laboratory Manual, John Innes Foundation, Norwich. UK, 1985) may be transformed.

In step (b), the transformants thus obtained are screened for the ability to take up carminomycin, convert it to daunorubicin, and excrete daunorubicin. Clones able to convert carminomycin to daunorubicin are identified by chromatographic analysis of extracts of a culture medium containing carminomycin for the presence of daunorubicin. Such clones are isolated and recombinant vectors contained therein are extracted: On digestion of the recombinant vectors with suitable restriction enzymes in step (c), the *S. peucetius* 29050 DNA inserted into each vector may be identified, sized and mapped. In this way, it may be checked that the vector contains an insert DNA of the invention.

Further, two or more overlapping inserts may be isolated that are wholly or partly embraced within the DNA of the invention. These may be fused together by cleavage at a common restriction site add subsequent ligation to obtain a DNA of the invention, pared in length using appropriate restriction enzymes if necessary. Restriction fragments of an insert DNA that contains a gene coding for the COMT protein may be obtained in step (d) also by cleaving an insert DNA with an appropriate restriction enzyme.

DNA of the invention may be mutated in a way thief, does not affect its ability to confer the ability to convert carminomycin to daunorubicin. This can be achieved by site-directed mutagenesis for example. Such mutated DNA forms part of the invention.

The DNA of the invention may also be incorporated into vectors suitable for expression of the dnrK gene in a non-streptomycete host like *E. coli*.

The following examples illustrate the invention.

Materials and Methods

Bacterial strains and plasmids: *E. coli* strain DH5α, which is sensitive to ampicillin and apramycin, is used for subcloning DNA fragments and *E. Coli* K38/Russel & Modet, *J. Bacteriol.* 159:1034 (1984/is used for expression of the *S. peucetius* dnrK gene. *E. coli* JM105 is used for making single stranded DNA for sequencing the dnrK gene.

Media and buffers: *E. coli* DH5α is maintained on LB agar (Sambrook et al., *Molecular Cloning. A Laboratory Manual*, 2nd ed. Cold Spring Harbor Press, Cold Spring Harbor, N.Y., 1989.) When selecting for transformants, ampicillin apramycin are added at concentrations of 50 μg/ml and 100 μg/ml, respectively. *E. coli* JM105 is maintained on M9 minimal agar medium (Sambrook et al., *Molecular Cloning. A Laboratory Manual*, 2nd ed. Cold Spring Harbor Press, Cold Spring Harbor. N.Y. 1989), and a colony is transferred to LB medium and grown overnight at 37° C. to obtain the bacteria used in the preparation of single stranded DNA. H agar (Sambrook et al., *Molecular Cloning. A Laboratory Manual.* 2nd ed. Cold Spring Harbor Press, Cold Spring Harbor, N.Y., 1989) is used to plate *E. coli* DH5α transformed with the replicative form of M13 DNA [(Yansch-Perron et al., *Gene* 33:103 (1985)]. *S. lividans* is maintained on R2YE agar (Hopwood et al., *Genetic Manipulation of Streptomyces. A Laboratory Manual*, John Innes Foundation, Norwich, UK, 1985) for the preparation or spores as well as for the regeneration of protoplasts.

Subcloning DNA fragments: DNA samples are digested with appropriate restriction enzymes and separated on agarose gels by standard methods (Sambrook et al., *Molecular Cloning. A Laboratory Manual,* 2nd ed. Cold Spring Harbor Press, Cold Spring Harbor, N.Y., 1989). Agarose slices containing DNA fragments of interest are excised from a gel and the DNA is isolated from these slices using the GENECLEAN device (Bio101, La Jolla, Calif.). The isolated DNA fragments are subcloned using standard techniques (Sambrook et al., *Molecular Cloning. A Laboratory Manual*, 2nd ed. Cold Spring Harbor Press, Cold Spring Harbor, N.Y., 1989) into *E. coli* and *E. coli*/Streptomyces shuttle vectors for biotransformation and expression experiments, respectively, and into M13 vectors [(Yansch-Perron et al., *Gene* 33:103 (1985)] for sequencing.

DNA sequencing: After subcloning DNA fragments of interest into an M13 vector, single stranded DNA is prepared by standard techniques (Sambrook et al., *Molecular Cloning. A Laboratory Manual*, 2nd ed. Cold Spring Harbor Press, Cold Spring Harbor, N.Y., 1989) and used in sequencing. DNA sequence data are obtained using a Sequenase version 2.0 sequencing kit (US Biochemicals, Cleveland, Ohio) according to the manufacturers suggestions. 7-Deaza dGTP is used instead of dGTP to avoid compressions. Initially, an universal primer of the M13 vector is used to obtain the sequence of the first 200-250 bases, then from these sequence data, an 17-mer oligoncleotide is synthesised using an Applied Biosystems 391 DNA synthesizer according to the manufacturer's directions and used as a primer to continue DNA sequencing until the complete DNA sequence data are obtained.

Transformation of Streptomyces species and *E. coli*: Competent cells of *E. coli* are prepared by the calcium chloride method (Sambrook et al., *Molecular Cloning. A Laboratory Manual*, 2nd ed. Cold Spring Harbor Press, Cold Spring Harbor, N.Y., 1989) and transformed by standard techniques (Sambrook et al., *Molecular Cloning. A Laboratory Manual*, 2nd ed. Cold Spring Harbor Press, Cold Spring Harbor, N.Y., 1989). *S. lividans* TK24 mycelium is grown in YEME medium (Hopwood et al., *Genetic Manipulation of Streptomyces. A Laboratory Manual*, John Innes Foundation, Norwich, UK, 1985) and harvested after 48 hr. The mycelial pellet is washed twice with 10.3% sucrose solution and used to prepare protoplasts according to the method outlined in the Hopwood manual (Hopwood et al., *Genetic Manipulation of Streptomyces. A Laboratory Manual*, John Innes Foundation, Norwich, UK, 1985). The protoplast pellet is suspended in about 300 microliters of P buffer (Hopwood et al., *Genetic Manipulation of Streptomyces. A Laboratory Manual*, John Innes Foundation, Norwich, UK, 1985) and a 50 microliter aliquot of this suspension is used for each transformation. Protoplasts are transformed with plasmid DNA according to the small-scale transformation method of Hopwood et al. (Hopwood et al., *Genetic Manipulation of Streptomyces. A Laboratory Manual*, John Innes Foundation, Norwich, UK, 1985). After 17 hr of regeneration on R2YE medium at 30° C., the plates are overlayed with 50 μg/ml of thiostrepton and allowed to grow at 30° C. until sporulated.

Bioconversion of carminomycin to daunorubicin: *S. lividans* transformants harboring different plasmids are inoculated into liquid R2YE medium (Hopwood et al., *Genetic Manipulation of Streptomyces. A Laboratory Manual*, John Innes Foundation, Norwich, UK, 1985) containing 5 μg/ml of thiostrepton. After 2 days of growth at 30° C., 2.5 ml of this culture is transferred to 25 ml of Strohl medium [(Dekleva et al., Can *J. Microbiol.* 31:287 (1985) containing 20 μg/ml of thiostrepton. Cultures are grown in baffled Erlenmeyer flasks on a rotary shaker at 300 rpm at 30° C. for 72 hr, after which carminomycin (as a solution in water at a concentration of 10 milligrams/ml) is added to cultures to give a final concentration of 5 µg/ml. After 24 h of further incubation on the shaker, the cultures are incubated in a water bath at 60° C. for 45 rain after the addition of 150 milligrams/ml of oxalic acid to hydrolize the glycosidic forms of the anthracycline metabolites. The metabolites are extracted from the cultures with 15 ml of chloroform after adjusting the pH of cultures to 8.4–8.6. The chloroform solution is filtered through a 0.45 µm Acrodisc CR filter (Gelman Sciences, Ann Arbor, Mich.) and 100 microliters of this filtrate is analyzed by HPLC on a Waters Nova-Pak $C_{18}$ cartridge (8 mm×10 cm) with a mobile phase of methanol-water (85:15) adjusted to pH 2.5 with phosphoric acid at a flow rate of 3 ml/min. The column output was monitored using Waters 6000 solvent delivery system, a 441 UV detector operated at 254 nm, and a 740 data module. Carminomycin and daunorubicin (10 µg/ml in methanol) were used as external standards to quantitate the amount of these metabolites isolated from the cultures.

Example 1

Cloning of the dnrK gene encoding carminomycin 4-O-methyltransferase

Several of the cosmid clones described by Stutzman-Engwall and Hutchinson [(*Proc. Natl. Acad. Sci. USA* 86:3135 (1989), representing approximately 96 kb of *S. peucetius* 29050 genomic DNA, are transformed into *S. lividans* TK24 and the transformants are analysed for the bioconversion of carminomycin to daunorubicin according to the method described in the materials and methods section. Cosmid clone pWHM339 [Otten et al., *J. Bacteriol.* 172:3427 (1990)] bioconverts 22% of added carminomycin to daunorubicin. A 11.2 kb EcoRI fragment from the insert in pWHM339 is subcloned into the cosmid vector pKC505 [Richardson et al., *Gene* 61:231 (1987)] to yield plasmid pWHM534. *S. lividans* TK24 transformed with pWHM534 shows a 25 to 60% bioconversion of added carminomycin to daunorubicin. A 5.8 kb SphI fragment from pWHM534 is subcloned in the SphI site of the high-copy number plasmid pWHM3 to yield the plasmid pWHM901. *S. lividans* transformed with pWHM901 exhibits a 50 to 85% bioconversion of carminomycin to daunorubicin. A 1.6 kb SphI/PvuII fragment is cloned from pWHM901 first into the SphI/SmaI sites of pUC19 [Yansch-Perron et al., *Gene* 33:103 (1985)], then the 1.6 kb DNA fragment is subcloned from the latter plasmid as an HindIII/EcoRI fragment into the HindIII/EcoI sites of pWHM3 to yield plasmid pWHM902 (FIG. 2). *S. lividans* transformed with pWHM902 bioconverts 100% of the carminomycin added to the culture to daunorubicin.

DNA sequence Of the region containing the dnrK gene

Figure 3A:
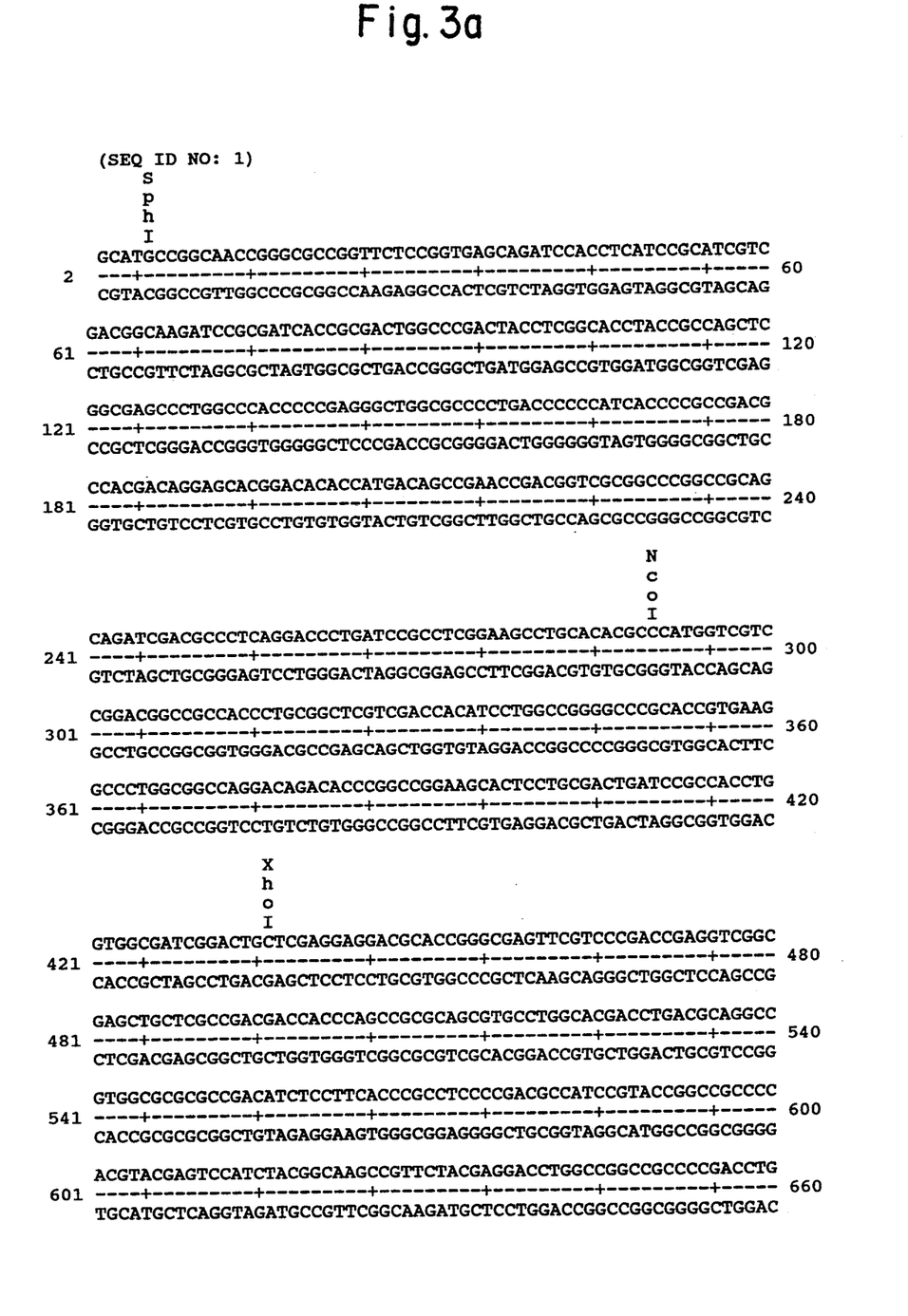
Figure 3C:
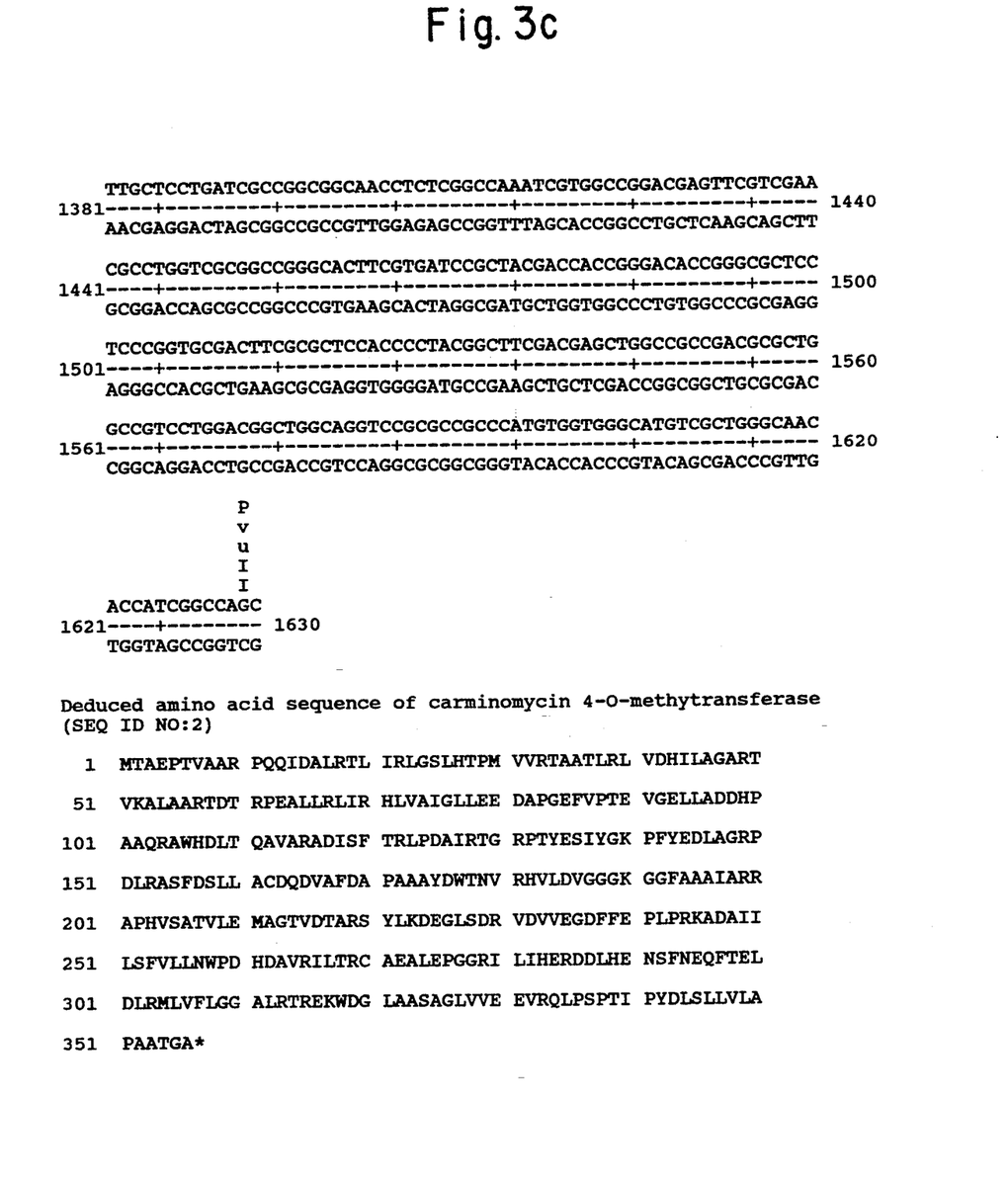

Sequencing a 2.5 kb DNA segment of the 5.8 kb SphI fragment in pWHM901 is carried out by subcloning. 0.4 kb SphI/XhoI, 0.7 kb XhoI/SstI, 0.6-kb SstI/SalI and 0.8 kb SalI/XhoI fragments from pWHN4902 into M13mp18 and -mp19 vectors [Yansch-Perron et al., *Gene* 33:103 (1985)] to obtain both orientations of each DNA segment. DNA sequencing of the resulting four clones is performed as described in the materials and methods section. The resulting DNA sequence of a 1.6 kb DNA fragment containing the dnrK gene, and the amino acid sequence of the COMT protein deduced by analysis of this DNA sequence with the CODON PREFERENCE program described by Devereux et al. [*Nucl. Acids Res.* 12:387 (1984)], are shown in FIG. 3. The dnrK open reading frame identified by CODON-PREFERENCE and TRANSLATE analysis [Deveraux et al., *Nucl. Acids Res.* 12:387 (1984)] codes for the COMT protein.

Example 2

Construction of a vector for expression of the dnrK gene in *E. coll*

An approx. 1.6 kb SphI/PvuII DNA fragment containing the entire dnrK open reading frame along with some flanking sequence (FIG. 3) is subcloned into SphI and SmaI-digested pUC19 [Yansch-Perron et al., *Gene* 33:103 (1985)] to give the plasmid pWHM904 (not shown). The following two oligodeoxynucleotide primers, corresponding to sequences on either side of the dnrK-containing fragment to be amplified, are synthesized with an Applied Biosystems 391 DNA synthesizer according to the manufacturer's directions:

```
         XbaI    BamHI    rbs            NdeI                                          (SEQ ID NO:3)
5' - GGG TCTABA GGATCC  AGGAG   CAG CATATG ACC GCT GAA CCG ACC GTC GCG GCC CGG CCG CAG CAG AT - 3': Primer #1
           SphI     PstI                                              (SEQ ID NO:4)
3' - AC CGC TAG CCT GAC GAG CTC CTC CGTACG GACGTC CCC - 5': Primer #2
```

The third postion of second, third and sixth codons (indicated by bold face letters) of the dnrK gene is changed by using primer #1 to reflect the most frequently used codon in highly expressed *E. coli* genes as a means to enhance the expression of the dnrK gene in *E. coli*:

ATG ACC GCT GAA CCG ACC GTC GCG
GCC CGG CCG CAG CAGA: Mutated
sequence (SEQ ID NO:5)

ATG ACB GCC GAA CCG ACG GTC GCG
GCC CGG CCG CAG CAGA: Wild type
sequence (SEQ ID NO:6)

Figure 4:
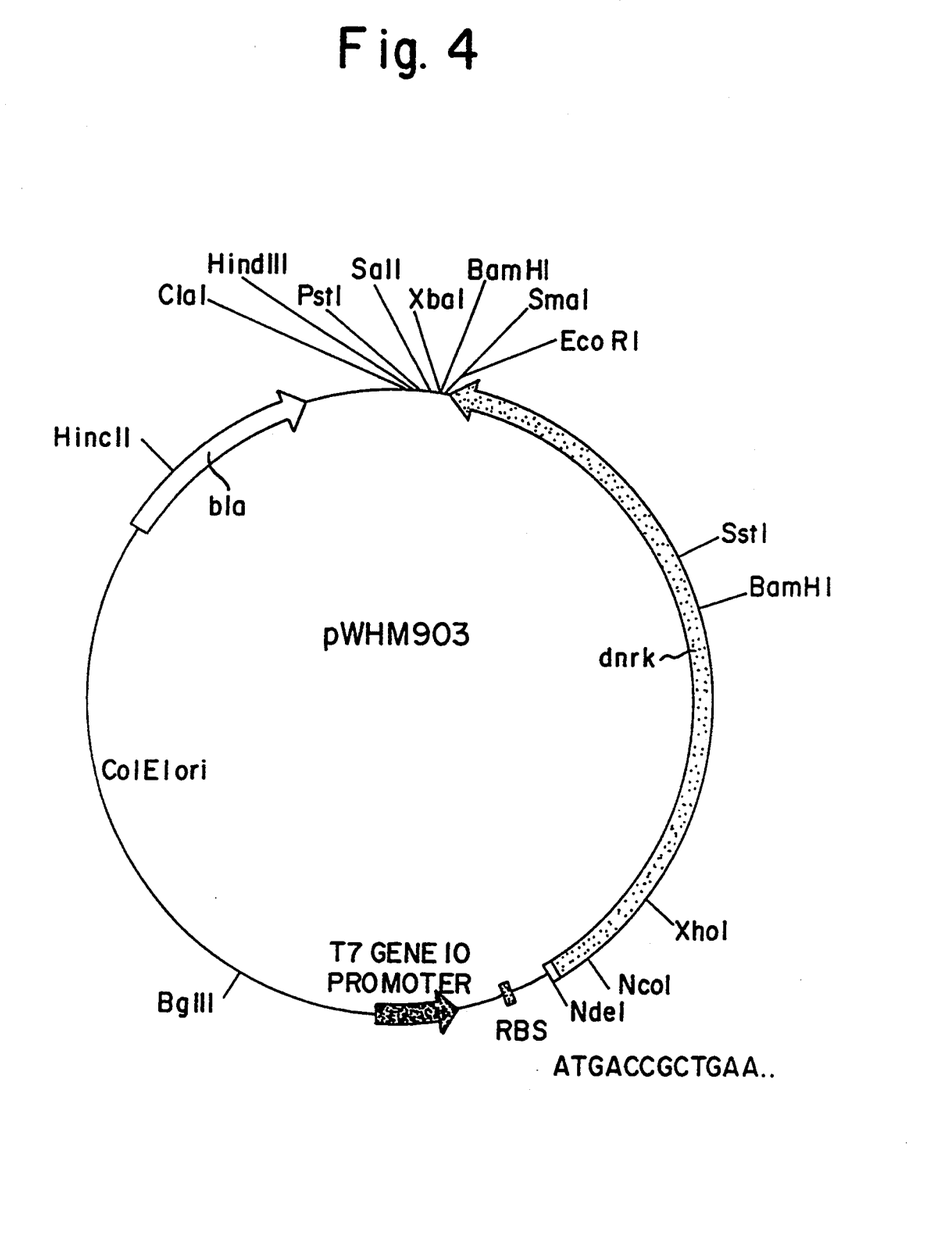
FIG. 4 is the restriction map analysis of the second DNA of the invention. This is an insert in recombinant plasmid pWHM903 that was constructed by insertion of a ≈ 1.4 kb NdeI/EcoRI DNA fragment, obtained from the 5.8 kb SphI DNA fragment of pWHM901 by site-directed mutagenesis, into the NdeI and EcoRI sites of the pT7-7 E. coli expression plasmid vector [Tabor and Richardson, Proc. Natl. Acad. Sci. USA 82:1074 (1985)]. The map shown in FIG. 4 does not necessarily provide an exhaustive listing of all restriction sites present in the DNA segment. However, the reported sites are sufficient for an unambiguous recognition of the segments.

These two primers are used to amplify the dnrK sequence of pWHM904 from nucleotides 205 (the beginning of the dnrK Off) to 445 of FIG. 3 by standard methods for the polymerase chain reaction with Streptormyces DNA [for example, see Guilfoile and Hutchinson, *J. Bacteriol.* 174:3659 (1992)]. From the amplified product, an 88 bp NdeI/NcoI fragment is excised and ligated to a 1.3 kb NccI/EcoRI fragment (obtained from pWHM902), containing the remaining dnrK gene (FIGS. 2 & 3), and NdeI/EcoRI-digested pT7-7 [Tabor and Richardson, *Proc. Natl. Acad. Sci. USA* 82:1074 (1985)], which results in the fusion of the dnrK orf to the T7 gene 10 promoter of this *E. coli* expression vector. Competent cells of *E. coli* DH5α are transformed with the ligated DNA and transformants were screened for pt7-7 with dnrK. The resulting plasmid is designated pWHM903 (FIG. 4).

Expression of the dnrK gene in *E. coli*

Competent *E. coli* cells containing the plasmid pGP1-2[Tabor and Richardson, Proc. selected on LB agar (Sambrook et al., *Molecular Cloning. A Laboratory Manual*, 2nd ed. Cold Spring Harbor Press, Cold Spring Harbor, N.Y., 1989) containing ampicillin (100 μg/ml) and kanamycin (50 μg/ml) after growth at 30° C. The procedure for preparing competent cells of *E. coli* containing pGP1-2 is the same as that for any other *E. coli* strain, except that the cultures are maintained at 30° C. instead of 37° C. Competent cells of *E. coli* containing pGP1-2 are prepared from cells grown at 30° C. to a OD$_{550}$ of 0.5 to 0.6 in LB medium containing kanamycin. ! t is very important to maintain strains containing DGP1-2 at 30° C. for routine maintainance and pre-induction growth to avoid over expression of T7 RNA polymerase which might otherwise result in a mutated plasmid.

A single transformant harboring both pGP1-2 and pWHM903 is inoculated into 25 ml of 2X YT medium (Sambrook et al., *Molecular Cloning. A Laboratory Manual*, 2nd ed. Cold Spring Harbor Press, Cold Spring Harbor, N.Y., 1989) containing 100 μg/ml ampicillin and 50 μg/ml kanamycin and grown overnight at 30° C. with vigorous agitation. The next morning cultures are heat shocked at 42° C. for 30 min in a shaking water bath and then transferred back to 30° C. After 90 min further incubation, one ml of the culture is centrifuged at 14,000 rpm in a microcentrifuge for 1 min, the supernatant is discarded, and the cell pellet is resuspended in 100 microliters of Laemmli buffer [Laemmli, *Nature* (London), 227:680 (1970)] and boiled for 5 min. The proteins contained in the boiled sample are analyzed on a 10% SDS-polyacrylamide gel using standard methods [Laemmli, *Nature* (London), 227:680 (1970)] by comparison with the proteins obtained from the cell extract of *E. coli* transformed with the pT7-7 vector that does not contain the dnrK gene. The COMT protein migrates at $M_r$ 38,700.

Example 3

Conversion of carminomycin to daunorubicin by a cell containing the COMT protein A single *E. coli* transformant harboring both pGP1-2 and pWHM903 was inoculated into 25 ml of 2 X YT medium containing 100 μg/ml ampicillin and 50 μg/ml kanamycin and grown overnight at 30° C. with vigorous agitation. The next morning cultures are heat shocked at 42° C. for 30 min in a shaking water bath and then transferred back to 30° C. after adding 5 μg/ml of carminomycin. The cultures are allowed to grow for additional 90 min, after which the anthracycline metabolites are isolated using standard methods and analysed on HPLC. Comparison of the relative areas of the signal peaks for carminomycin and daunorubicin in the HPLC chromatogram indicates that 75 to 80% of the carminomycin added to the culture medium is converted to daunorubicin.

---

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1632 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: CDS
        ( B ) LOCATION: 204..1271

( x i ) SEQUENCE DESCRIPTION: SEQ ID NO:1:

```
GCATGCCGGC AACCGGGCGC CGGTTCTCCG GTGAGCAGAT CCACCTCATC CGCATCGTCG      60

ACGGCAAGAT CCGCGATCAC CGCGACTGGC CCGACTACCT CGGCACCTAC CGCCAGCTCG     120

GCGAGCCCTG GCCCACCCCC GAGGGCTGGC GCCCCTGACC CCCCATCACC CCGCCGACGC     180

CACGACAGGA GCACGGACAC ACC ATG ACA GCC GAA CCG ACG GTC GCG GCC         230
                           Met Thr Ala Glu Pro Thr Val Ala Ala
                            1               5

CGG CCG CAG CAG ATC GAC GCC CTC AGG ACC CTG ATC CGC CTC GGA AGC       278
Arg Pro Gln Gln Ile Asp Ala Leu Arg Thr Leu Ile Arg Leu Gly Ser
 10              15                  20                  25

CTG CAC ACG CCC ATG GTC GTC CGG ACG GCC GCC ACC CTG CGG CTC GTC       326
Leu His Thr Pro Met Val Val Arg Thr Ala Ala Thr Leu Arg Leu Val
                 30                  35                  40

GAC CAC ATC CTG GCC GGG GCC CGC ACC GTG AAG GCC CTG GCG GCC AGG       374
Asp His Ile Leu Ala Gly Ala Arg Thr Val Lys Ala Leu Ala Ala Arg
             45                  50                  55
```

```
ACA GAC ACC CGG CCG GAA GCA CTC CTG CGA CTG ATC CGC CAC CTG GTG      422
Thr Asp Thr Arg Pro Glu Ala Leu Leu Arg Leu Ile Arg His Leu Val
        60                  65                  70

GCG ATC GGA CTG CTC GAG GAG GAC GCA CCG GGC GAG TTC GTC CCG ACC      470
Ala Ile Gly Leu Leu Glu Glu Asp Ala Pro Gly Glu Phe Val Pro Thr
    75                  80                  85

GAG GTC GGC GAG CTG CTC GCC GAC GAC CAC CCA GCC GCG CAG CGT GCC      518
Glu Val Gly Glu Leu Leu Ala Asp Asp His Pro Ala Ala Gln Arg Ala
90                  95                  100                 105

TGG CAC GAC CTG ACG CAG GCC GTG GCG CGC GCC GAC ATC TCC TTC ACC      566
Trp His Asp Leu Thr Gln Ala Val Ala Arg Ala Asp Ile Ser Phe Thr
                110                 115                 120

CGC CTC CCC GAC GCC ATC CGT ACC GGC CGC CCC ACG TAC GAG TCC ATC      614
Arg Leu Pro Asp Ala Ile Arg Thr Gly Arg Pro Thr Tyr Glu Ser Ile
            125                 130                 135

TAC GGC AAG CCG TTC TAC GAG GAC CTG GCC GGC CGC CCC GAC CTG CGC      662
Tyr Gly Lys Pro Phe Tyr Glu Asp Leu Ala Gly Arg Pro Asp Leu Arg
        140                 145                 150

GCG TCC TTC GAC TCG CTG CTC GCC TGC GAC CAG GAC GTC GCC TTC GAC      710
Ala Ser Phe Asp Ser Leu Leu Ala Cys Asp Gln Asp Val Ala Phe Asp
    155                 160                 165

GCT CCG GCC GCC GCG TAC GAC TGG ACG AAC GTC CGG CAT GTG CTC GAC      758
Ala Pro Ala Ala Ala Tyr Asp Trp Thr Asn Val Arg His Val Leu Asp
170                 175                 180                 185

GTG GGT GGC GGC AAG GGT GGT TTC GCC GCG GCC ATC GCG CGC CGG GCC      806
Val Gly Gly Gly Lys Gly Gly Phe Ala Ala Ala Ile Ala Arg Arg Ala
                190                 195                 200

CCG CAC GTG TCG GCC ACC GTG CTG GAG ATG GCG GGC ACC GTG GAC ACC      854
Pro His Val Ser Ala Thr Val Leu Glu Met Ala Gly Thr Val Asp Thr
            205                 210                 215

GCC CGC TCC TAC CTG AAG GAC GAG GGC CTC TCC GAC CGT GTC GAC GTC      902
Ala Arg Ser Tyr Leu Lys Asp Glu Gly Leu Ser Asp Arg Val Asp Val
        220                 225                 230

GTC GAG GGG GAC TTC TTC GAG CCG CTG CCC CGC AAG GCG GAC GCG ATC      950
Val Glu Gly Asp Phe Phe Glu Pro Leu Pro Arg Lys Ala Asp Ala Ile
    235                 240                 245

ATC CTC TCT TTC GTC CTC CTC AAC TGG CCG GAC CAC GAC GCC GTC CGG      998
Ile Leu Ser Phe Val Leu Leu Asn Trp Pro Asp His Asp Ala Val Arg
250                 255                 260                 265

ATC CTC ACC CGC TGC GCC GAG GCC CTG GAG CCC GGC GGG CGC ATC CTG     1046
Ile Leu Thr Arg Cys Ala Glu Ala Leu Glu Pro Gly Gly Arg Ile Leu
                270                 275                 280

ATC CAC GAG CGC GAC GAC CTC CAC GAG AAC TCG TTC AAC GAA CAG TTC     1094
Ile His Glu Arg Asp Asp Leu His Glu Asn Ser Phe Asn Glu Gln Phe
            285                 290                 295

ACA GAG CTC GAT CTG CGG ATG CTG GTC TTC CTC GGC GGT GCC CTG CGC     1142
Thr Glu Leu Asp Leu Arg Met Leu Val Phe Leu Gly Gly Ala Leu Arg
        300                 305                 310

ACC CGC GAG AAG TGG GAC GGC CTG GCC GCG TCG GCG GGC CTC GTG GTC     1190
Thr Arg Glu Lys Trp Asp Gly Leu Ala Ala Ser Ala Gly Leu Val Val
    315                 320                 325

GAG GAG GTG CGG CAA CTG CCG TCG CCG ACC ATC CCG TAC GAC CTC TCG     1238
Glu Glu Val Arg Gln Leu Pro Ser Pro Thr Ile Pro Tyr Asp Leu Ser
330                 335                 340                 345

CTC CTC GTC CTT GCC CCC GCG GCC ACC GGC GCC TGACACACGA GGTACGGGAA   1291
Leu Leu Val Leu Ala Pro Ala Ala Thr Gly Ala
                350                 355

GGGTTCATCA GCAATGCCGA CACGCATGAT CACCAACGAT GAGGTGACCC TGTGGAGCGA   1351

AGGGCTCGGC GATCCGGCCG ACGCCCCGTT GCTCCTGATC GCCGGCGGCA ACCTCTCGGC   1411

CAAATCGTGG CCGGACGAGT TCGTCGAACG CCTGGTCGCG GCCGGGCACT TCGTGATCCG   1471
```

-continued

```
CTACGACCAC CGGGACACCG GGCGCTCCTC CCGGTGCGAC TTCGCGCTCC ACCCCTACGG    1531
CTTCGACGAG CTGGCCGCCG ACGCGCTGGC CGTCCTGGAC GGCTGGCAGG TCCGCGCCGC    1591
CCATGTGGTG GGCATGTCGC TGGGCAACAC CATCGGCCAG C                        1632
```

( 2 ) INFORMATION FOR SEQ ID NO:2:

( i ) SEQUENCE CHARACTERISTICS:
        ( A ) LENGTH: 356 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Thr Ala Glu Pro Thr Val Ala Ala Arg Pro Gln Gln Ile Asp Ala
 1               5                  10                  15

Leu Arg Thr Leu Ile Arg Leu Gly Ser Leu His Thr Pro Met Val Val
            20                  25                  30

Arg Thr Ala Ala Thr Leu Arg Leu Val Asp His Ile Leu Ala Gly Ala
        35                  40                  45

Arg Thr Val Lys Ala Leu Ala Ala Arg Thr Asp Thr Arg Pro Glu Ala
    50                  55                  60

Leu Leu Arg Leu Ile Arg His Leu Val Ala Ile Gly Leu Leu Glu Glu
65                  70                  75                  80

Asp Ala Pro Gly Glu Phe Val Pro Thr Glu Val Gly Glu Leu Leu Ala
                85                  90                  95

Asp Asp His Pro Ala Ala Gln Arg Ala Trp His Asp Leu Thr Gln Ala
            100                 105                 110

Val Ala Arg Ala Asp Ile Ser Phe Thr Arg Leu Pro Asp Ala Ile Arg
        115                 120                 125

Thr Gly Arg Pro Thr Tyr Glu Ser Ile Tyr Gly Lys Pro Phe Tyr Glu
    130                 135                 140

Asp Leu Ala Gly Arg Pro Asp Leu Arg Ala Ser Phe Asp Ser Leu Leu
145                 150                 155                 160

Ala Cys Asp Gln Asp Val Ala Phe Asp Ala Pro Ala Ala Ala Tyr Asp
                165                 170                 175

Trp Thr Asn Val Arg His Val Leu Asp Val Gly Gly Gly Lys Gly Gly
            180                 185                 190

Phe Ala Ala Ala Ile Ala Arg Arg Ala Pro His Val Ser Ala Thr Val
        195                 200                 205

Leu Glu Met Ala Gly Thr Val Asp Thr Ala Arg Ser Tyr Leu Lys Asp
    210                 215                 220

Glu Gly Leu Ser Asp Arg Val Asp Val Val Glu Gly Asp Phe Phe Glu
225                 230                 235                 240

Pro Leu Pro Arg Lys Ala Asp Ala Ile Ile Leu Ser Phe Val Leu Leu
                245                 250                 255

Asn Trp Pro Asp His Asp Ala Val Arg Ile Leu Thr Arg Cys Ala Glu
            260                 265                 270

Ala Leu Glu Pro Gly Gly Arg Ile Leu Ile His Glu Arg Asp Asp Leu
        275                 280                 285

His Glu Asn Ser Phe Asn Glu Gln Phe Thr Glu Leu Asp Leu Arg Met
    290                 295                 300

Leu Val Phe Leu Gly Gly Ala Leu Arg Thr Arg Glu Lys Trp Asp Gly
305                 310                 315                 320

Leu Ala Ala Ser Ala Gly Leu Val Val Glu Glu Val Arg Gln Leu Pro
                325                 330                 335
```

```
Ser Pro Thr Ile Pro Tyr Asp Leu Ser Leu Leu Val Leu Ala Pro Ala
        340             345                 350

Ala Thr Gly Ala
        355
```

( 2 ) INFORMATION FOR SEQ ID NO:3:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:3:

```
GGGTCTAGAG GATCCAGGAG CAGCATATGA CCGCTGAACC GACCGTCGCG GCCCGGCCGC    60
AGCAGAT                                                              67
```

( 2 ) INFORMATION FOR SEQ ID NO:4:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:4:

```
ACCGCTAGCC TGACGAGCTC CTCCGTACGG ACGTCCCC                            38
```

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:5:

```
ATGACCGCTG AACCGACCGT CGCGGCCCGG CCGCAGCAGA                          40
```

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:6:

```
ATGACAGCCG AACCGACGGT CGCGGCCCGG CCGCAGCAGA                          40
```

We claim:

1. An isolated and purified carminomycin 4-O-methyl transferase consisting essentially of the amino acid sequence: (SEQ ID NO: 2)

```
  1 MTAEPTVAAR PQQIDALRTL IRLGSLHTPM
    VVRTAATLRL VDHILAGART
 51 VKALAARTDT RPEALLRLIR HLVAIGLLEE
    DAPGEFVPTE VGELLADDHP
101 AAQRAWHDLT QAVARADISF TRLPDAIRTG
    RPTYESIYGK PFYEDLAGRP
151 DLRASFDSLL ACDQDVAFDA PAAAYDWTNV
    RHVLDVGGGK GGFAAAIARR
201 APHVSATVLE MAGTVDTARS YLKDEGLSDR
```

-continued

```
              VDVVEGDFFE PLPRKADAII
251 LSFVLLNWPD HDAVRILTRC AEALEPGGRI
              LIHERDDLHE NSFNEQFTEL
```

-continued

```
301 DLRMLVFLGG ALRTREKWDG LAASAGLVVE
              EVRQLPSPTI PYDLSLLVLA
351 PAATGA.
```

* * * * *